Figure 1:
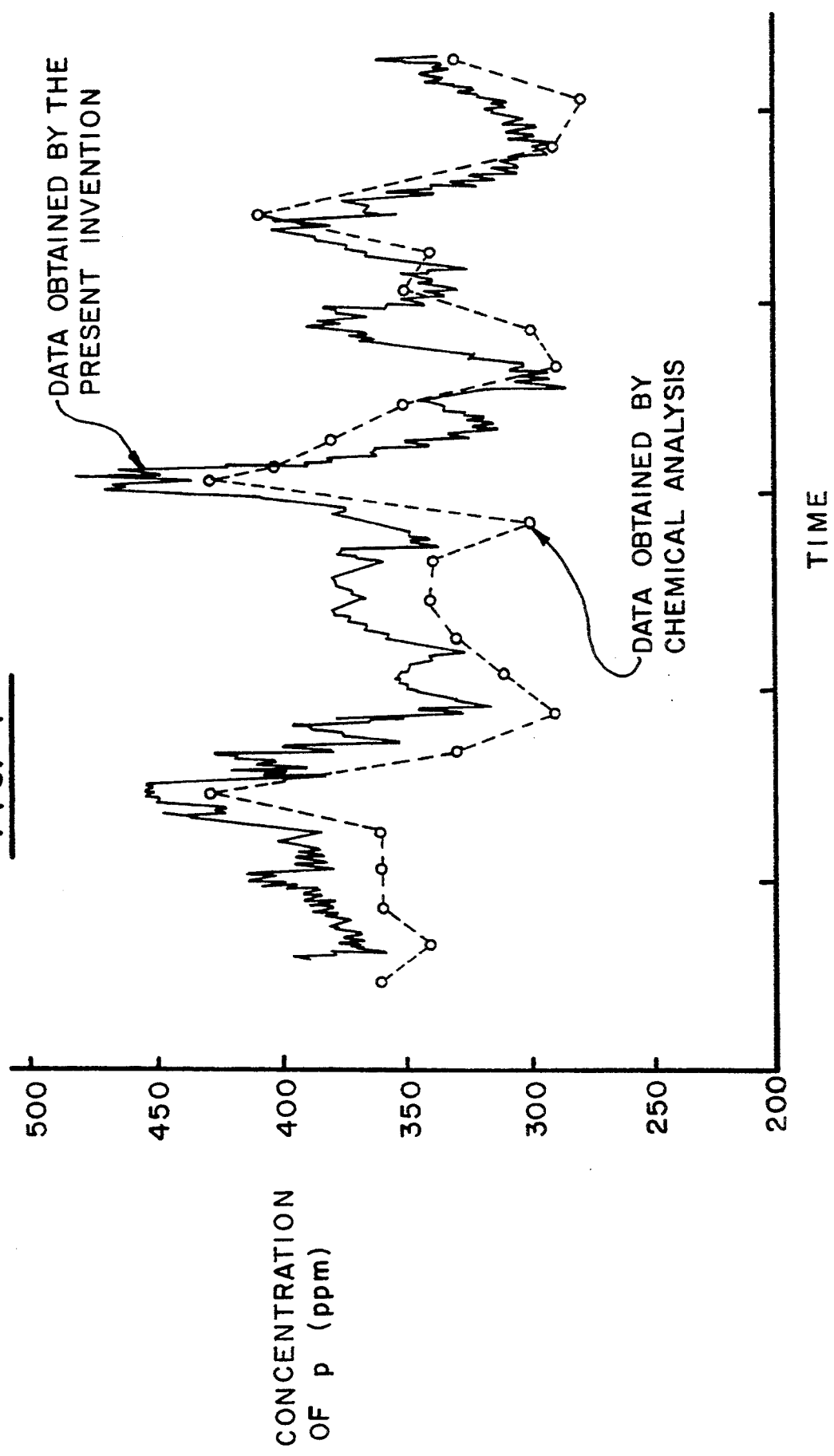

United States Patent [19]

Kimura et al.

[11] Patent Number: 5,432,458
[45] Date of Patent: Jul. 11, 1995

[54] PROCESS FOR DETERMINATION OF PHOSPHORUS IN MOLTEN COPPER

[75] Inventors: Etsuji Kimura; Yasuhiro Hanaue, both of Omiya, Japan

[73] Assignee: Mitsubishi Materials Corporation, Japan

[21] Appl. No.: 721,132

[22] Filed: Jun. 26, 1991

[30] Foreign Application Priority Data

Jun. 29, 1990 [JP] Japan ................... 2-172385

[51] Int. Cl.⁶ .................. G01R 27/02; G01N 27/00
[52] U.S. Cl. ................... 324/693; 324/71.1
[58] Field of Search .......... 324/693, 71.1; 164/4.1; 266/99

[56] References Cited

U.S. PATENT DOCUMENTS 5,192,404  3/1993  Fray et al. ............... 204/153.19

Primary Examiner—Maura K. Regan
Attorney, Agent, or Firm—Webb Ziesenheim Bruening Logsdon Orkin & Hanson

[57] ABSTRACT

Phosphorus concentration in molten copper can be determined by measuring temperature and electric resistivity of molten copper.

3 Claims, 1 Drawing Sheet

PROCESS FOR DETERMINATION OF PHOSPHORUS IN MOLTEN COPPER

FIELD OF THE INVENTION

This invention relates to a continuously applicable rapid process for determination of phosphorus in molten copper especially suitably for copper smelting or copper casting.

BACKGROUND OF THE INVENTION

Determination of phosphorus in molten copper traditionally depends upon chemical or instrumental analysis of solidified samples. The conventional method lacks rapidness and, therefore, is not advantageous from the viewpoint of process control.

Recently, a proposal has been made to determine phosphorus concentration in molten metal (principally iron) by creating an equilibrium between oxygen and phosphorus in the molten metal, determining the activity of oxygen by means of an electrode of a solid electrolyte and calculating the phosphorus concentration (Japanese Laid-Open Patent Publication (Kokai) No. 61-260157). However, it is thought that this method is practically accompanied by considerably difficulty for stabilization of the equilibrium state when it is applied in the commercial production of copper.

Estimation of the phosphorus concentration in copper by measurement of the electric resistance of solid copper materials has hitherto been attempted. However, accurate measurement is not yet achieved since electric resistivity of solid copper is influenced by its metallographical structure and preparation of specimens for accurate measurement of electric resistivity requires an elaborate work.

The measurement of electric resistivity of molten copper, has been attempted since olden days from academic interest. The investigation exclusively relates to pure copper and there is not report relating to phosphorus concentration. Also, technique of the measurement is difficult since high temperature molten metal is handled. Therefore, there has been no report relating to the determination of a specific impurity in molten copper by measurement of electric resistance.

We considered:

(1) Molten metal is free from influence of metallographical structure and is suitable for continuous measurement since shaping, polishing etc. for preparation of specimens are not required. Therefore, rapid and accurate analysis is possible with molten samples, if a technique of measurement is established.

(2) In the academic research, measurement is carried out using a small amount of sample and taking much time. Therefore, it is unavoidable that the sample is contaminated with the material of the electrode and the temperature distribution does not easily become uniform in a small apparatus. These facts will cause errors in measurement. To the contrary, however, an accurate measurement of resistivity would be possible if a large amount of sample can be handled.

(3) The copper deoxidized with phosphorus contains little impurities other than phosphorus. When the phosphorusdeoxidized copper is considered, it can be regarded that the electric resistivity is determined by phosphorus concentration and temperature.

Led by the above-described presupposition, we investigated the relation of phosphorus concentration and temperature with respect to phosphorus-deoxidized copper, containing 0–1000 ppm phosphorus in a temperature range of 1083°–1250° C., and found that there is a relation between phosphorus concentration, electric resistivity and temperature:

$$\rho = AT + BX + C$$

wherein A, B and C are constants; p is electric resistivity of molten copper, X is phosphorus concentration and T is temperature. A, B and C are determined for each apparatus.

SUMMARY OF THE INVENTION

The present invention provides a process for determining phosphorus concentration in molten copper which comprises simultaneously measuring the temperature and electric resistivity of molten copper and calculating the phosphorus concentration from the relation:

$$\rho = AT + BX + C$$

wherein $\rho$ is electric resistivity of molten copper, T is temperature of molten copper, X is phosphorus concentration, and A, B and C are constants which are experimentally determined with respect to copper samples of which phosphorus concentrations are known for each apparatus used.

The process of the present invention is applicable to so-called phosphorus-deoxidized copper and coppers equivalent thereto; that is, copper which contains not more than 50 ppm of oxygen and not more than 200 ppm of other elements. It is iron that influences the resistivity of molten copper most. Therefore, if the tolerable errors of the phosphorus concentration is considered to be about 100 ppm, the iron concentration must be not more than 200 ppm. If the contents of other elements are known by other methods, however, larger amounts of the impurity element may be present.

Practically, it is advantageous to measure resistivity and temperature of molten copper in the distributor (tundish or reservoir for molten metal provided immediately above the mold) in the case of continuous casting for instance. In the distributor, the temperature distribution is very small and errors in the temperature measurement is minimum. Also, the sample immediately before casting is analyzed, and, therefore, the measured phosphorus concentration is equal to that of the cast product or very close thereto, if not equal. Therefore, the process is very useful for quality control in continuous casting of copper.

BRIEF DESCRIPTION OF THE ATTACHED DRAWING

FIG. 1 is a graph showing phosphorus concentrations determined by the process of the present invention and those by chemical analysis in comparison.

SPECIFIC DISCLOSURE OF THE INVENTION

The invention will now be described by way of basic experiment and working examples.

Temperature and electric resistivity of phosphorus-deoxidized copper samples containing different concentrations of phosphorus were measured by the known four terminal method. The results are shown in Table 1. From these results the following relation was determined by regression analysis as follows:

$$\rho = 0.0085T + 0.0021X + 11.5$$

wherein the electric resistivity is in $\mu\Omega cm$, the temperature T is in °C. and the phosphorus concentration is in ppm. The coefficients are characteristic to the apparatus used but the relation can be generalized to $$\rho = AT + BX + C$$

Example

In the continuous casting of phosphorus-deoxidized copper, the phosphorus concentration was measured in the distributor in accordance with the present invention. Simultaneously, samples were taken periodically for the precise chemical analysis. The results are shown in the attached FIG. 1.

It is apparent that the process of the present invention determines the phosphorus concentration with accuracy comparable to that of chemical analysis.

TABLE 1

| Temperature (°C.) | Known conc. of P (ppm) | El. Resistivity ($\mu\Omega$cm) |
|---|---|---|
| 1131 | 42 | 21.24 |
| 1132 | 78 | 21.35 |
| 1134 | 125 | 21.44 |
| 1133 | 169 | 21.54 |
| 1133 | 221 | 21.64 |
| 1133 | 271 | 21.74 |
| 1133 | 326 | 21.84 |
| 1133 | 373 | 21.94 |
| 1133 | 418 | 22.04 |
| 1115 | 50 | 21.12 |
| 1114 | 98 | 21.22 |
| 1114 | 138 | 21.32 |
| 1114 | 188 | 21.41 |
| 1115 | 239 | 21.53 |
| 1114 | 290 | 21.61 |
| 1113 | 340 | 21.74 |
| 1113 | 412 | 21.83 |
| 1112 | 450 | 21.93 |
| 1144 | 59 | 21.36 |
| 1145 | 85 | 21.45 |
| 1145 | 129 | 21.56 |
| 1145 | 168 | 21.65 |
| 1144 | 214 | 21.73 |

TABLE 1-continued

| Temperature (°C.) | Known conc. of P (ppm) | El. Resistivity ($\mu\Omega$cm) |
|---|---|---|
| 1144 | 263 | 21.86 |
| 1144 | 304 | 21.92 |
| 1144 | 354 | 22.02 |
| 1145 | 406 | 22.18 |
| 1135 | 95 | 21.38 |
| 1135 | 141 | 21.49 |
| 1135 | 192 | 21.6 |
| 1334 | 235 | 21.68 |
| 1134 | 294 | 21.78 |
| 1134 | 336 | 21.9 |
| 1134 | 388 | 22.01 |
| 1134 | 432 | 22.09 |
| 1115 | 39 | 21.15 |
| 1115 | 78 | 21.21 |
| 1115 | 123 | 21.31 |
| 1113 | 166 | 21.39 |
| 1113 | 212 | 21.48 |
| 1115 | 263 | 21.6 |
| 1115 | 293 | 21.66 |
| 1115 | 368 | 21.79 |
| 1115 | 429 | 21.91 |

We claim:

1. A method for determining phosphorous concentration in molten copper, said process comprising the steps of:
   a) utilizing a copper sample of which the phosphorous concentration is known to experimentally determine constants which relate the phosphorous concentration to temperature and electrical resistivity of the molten copper according to the relation
   $$= AT + BX + C$$
   wherein is electrical resistivity, T is temperature, X is phosphorous concentration, and A, B, and C are said constants;
   b) measuring the temperature of said molten copper;
   c) measuring the electrical resistivity of said molten copper simultaneously with said measuring of the temperature of said molten copper; and
   d) determining the phosphorous concentration in said molten copper based upon said relation and said measured temperature and electrical resistivity and said constants.

2. The method as recited in claim 4, wherein said measurement of temperature and electric resistivity is conducted in the distributor of a continuous casting of copper.

3. The method as recited in claim 2, wherein said measurement of electric resistivity is conducted by four terminal method.

* * * * *

UNITED STATES PATENT AND TRADEMARK OFFICE
CERTIFICATE OF CORRECTION

PATENT NO. : 5,432,458
DATED : July 11, 1995
INVENTOR(S) : Etsuji Kimura et al

It is certified that error appears in the above-indentified patent and that said Letters Patent is hereby corrected as shown below:

Column 1 Line 67 "phosphorusdeoxidized" should read --phosphorus-deoxidized--.

Column 2 Line 13 "p" should read --$\rho$--.

Column 3 Line 7 "11.5" should read --11.55--.

Claim 2 Line 45 Column 4 "claim 4," should read --claim 1,--.

Signed and Sealed this

Twenty-eighth Day of November 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,432,458
DATED : July 11, 1995
INVENTOR(S) : Etsuji Kimura and Yasuhiro Hanaue It is certified that error appears in the above-indentified patent and that said Letters Patent is hereby corrected as shown below:

Claim 1 Line 33 Column 4 " =AT+BX+C" should read --$\rho$=AT+BX+C--.

Claim 1 Line 34 Column 4 "wherein   is" should read --wherein $\rho$ is--.

Signed and Sealed this

Thirteenth Day of August, 1996

Attest:

BRUCE LEHMAN

Attesting Officer         Commissioner of Patents and Trademarks